(12) United States Patent
Weerasooriya et al.

(10) Patent No.: US 8,372,788 B2
(45) Date of Patent: Feb. 12, 2013

(54) STYRYLPHENOL ALKOXYLATE SULFATE AS A NEW SURFACTANT COMPOSITION FOR ENHANCED OIL RECOVERY APPLICATIONS

(75) Inventors: Upali P. Weerasooriya, Austin, TX (US); Gary A. Pope, Cedar Park, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 2 days.

(21) Appl. No.: 13/015,761

(22) Filed: Jan. 28, 2011

(65) Prior Publication Data

US 2011/0190174 A1    Aug. 4, 2011

Related U.S. Application Data

(60) Provisional application No. 61/298,955, filed on Jan. 28, 2010.

(51) Int. Cl.
*C09K 8/584* (2006.01)
*C09K 8/588* (2006.01)

(52) U.S. Cl. ........ 507/254; 507/260; 507/261; 507/263; 507/268; 507/276; 558/34; 166/305.1

(58) Field of Classification Search .................. 507/254, 507/231, 261, 262, 904, 935; 525/333.3, 525/333.5; 558/34
See application file for complete search history.

(56) References Cited

U.S. PATENT DOCUMENTS

| | | | |
|---|---|---|---|
| 4,842,776 A | 6/1989 | Schmidt et al. | |
| 4,943,299 A | 7/1990 | Schulze et al. | |
| 5,082,591 A | 1/1992 | Marchetto et al. | |
| 5,104,983 A | 4/1992 | Stock et al. | |
| 7,884,056 B2 * | 2/2011 | Bendejacq et al. | 507/219 |
| 2002/0058697 A1 | 5/2002 | Moore et al. | |
| 2009/0076202 A1 * | 3/2009 | Seibold et al. | 524/156 |
| 2009/0270281 A1 | 10/2009 | Steinbrenner et al. | |

FOREIGN PATENT DOCUMENTS

| | | | |
|---|---|---|---|
| WO | WO 2007117512 A1 * | 10/2007 | |
| WO | WO 2008/079855 A2 | 7/2008 | |
| WO | WO 2009/021985 A2 | 2/2009 | |

OTHER PUBLICATIONS

International Search Report and Written Opinion dated Apr. 2, 2011 for International PCT Application No. PCT/US2011/022770, 14 pages.
Yonghua, Z.G.G. et al., "Synthesis and properties of ammonium tristyrylphenol poloxyethylene ether sulfate", Advances in Fine Petrochemicals 12:17-21, 2002, Abstract only, 1 page.

* cited by examiner

*Primary Examiner* — John J Figueroa
(74) *Attorney, Agent, or Firm* — Kilpatrick Townsend & Stockton LLP

(57) ABSTRACT

A method of making a styryl phenol alkoxylate sulfate surfactant by alkoxylation of a styryl phenol using propylene oxide (PO) and/or ethylene oxide (EO) followed by a sulfation reaction. The styrylphenol alkoxylate sulfate surfactant of the present invention is made by a facile and inexpensive method. The large hydrophobe surfactants of the present invention find uses in EOR applications where it is used for solubilization and mobilization of oil optionally containing asphaltene, and for environmental cleanup. Further, the unsulfated version of the large hydrophobe styrylphenol alkoxylate surfactant of the present invention can be used as an ultra-high molecular weight non-ionic surfactant.

61 Claims, 2 Drawing Sheets

STYRYLPHENOL ALKOXYLATE SULFATE AS A NEW SURFACTANT COMPOSITION FOR ENHANCED OIL RECOVERY APPLICATIONS

CROSS-REFERENCE TO RELATED APPLICATIONS

This application claims priority to U.S. Provisional Application Ser. No. 61/298,955, filed Jan. 28, 2010, the entire contents of which are incorporated herein by reference.

TECHNICAL FIELD OF THE INVENTION

The present invention relates in general to the field of oil recovery, and more particularly, to a surfactant composition comprising styrylphenol alkoxylate sulfate and derivatives for enhanced oil recovery (EOR) applications.

STATEMENT OF FEDERALLY FUNDED RESEARCH

None.

REFERENCE TO A SEQUENCE LISTING

None.

BACKGROUND OF THE INVENTION

Without limiting the scope of the invention, its background is described in connection with methods of manufacture and use of large hydrophobe surfactants and related compounds for oil recovery applications.

U.S. Pat. No. 4,842,776 issued to Schmidt et al. (1989) discloses Styrylaryloxy ether sulfonates of the formula:

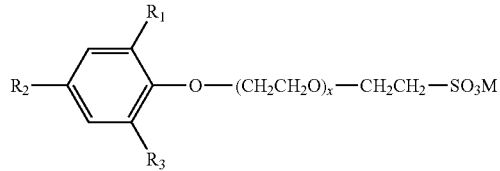

in which either $R_1$ denotes styryl and simultaneously $R_2$ and $R_3$ are identical or different and denote hydrogen or styryl, or $R_1$ and $R_2$ are nonidentical and each denote methyl or styryl and simultaneously $R_3$ denotes hydrogen or styryl, x denotes a number from 2 to 20, and M denotes an ammonium or alkali metal cation. These compounds are suitable as surfactant auxiliaries in oil recovery.

WIPO Patent Application WO/2008/079855 (Raney and Schmidt, 2008) describes compositions and methods of treating a hydrocarbon containing formation, comprising: (a) providing a composition to at least a portion of the hydrocarbon containing formation, wherein the composition comprises a secondary alcohol derivative; and (b) allowing the composition to interact with hydrocarbons in the hydrocarbon containing formation. The invention further describes a composition produced from a hydrocarbon containing formation, comprising hydrocarbons from a hydrocarbon containing formation and a secondary alcohol derivative.

U.S. Patent Application No. 20090270281 (Steinbrenner et al., 2009) describes the use of a surfactant mixture comprising at least one surfactant having a hydrocarbon radical composed of from 12 to 30 carbon atoms and at least one co-surfactant having a branched hydrocarbon radical composed of from 6 to 11 carbon atoms for tertiary mineral oil extraction. According to the Steinbrenner invention, the surfactants (A) are used in a mixture with at least one co-surfactant (B) which has the general formula $R^2$—O—$(R^3$—O$)_n$—$R^4$, where the $R^2$, $R^3$ and $R^4$ radicals and the number n are each defined as follows: n is from 2 to 20, $R^2$ is a branched hydrocarbon radical which has from 6 to 11 carbon atoms and an average degree of branching of from 1 to 2.5, $R^3$ are each independently an ethylene group or a propylene group, with the proviso that the ethylene and propylene groups—where both types of groups are present—may be arranged randomly, alternately or in block structure, $R^4$ is hydrogen or a group selected from the group of —$SO_3H$, —$PO_3H_2$, —$R^5$—COOH, —$R^5$—$SO_3H$ or —$R^5$—$PO_3H_2$ or salts thereof, where $R^5$ is a divalent hydrocarbon group having from 1 to 4 carbon atoms.

SUMMARY OF THE INVENTION

The present invention describes compositions and methods of manufacture of styrylphenol alkoxylate sulfate surfactants where in the number of styryl groups could be anywhere from 2-3, for enhanced oil recovery (EOR) and other commercially important applications.

In one embodiment the present invention discloses an alkoxy sulfate surfactant composition, wherein the alkoxy sulfate comprise one or more, poly propoxy groups (PO), poly ethoxy groups (EO) or both and a sulfate group of formula (I), comprising

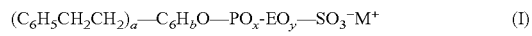

wherein a=3, b=2, a=2, b=3 or a=2-3, b=3-2, wherein, x corresponds to the number of propoxy groups and ranges from 0 to 50, y corresponds to the number of ethoxy groups and ranges from 0 to 100, and M is a counter ion to the sulfate group, wherein M is selected from the group consisting of Na, K, Mg, Ca, and $NH_4$. The composition of formula (I) is adapted for enhanced oil recovery (EOR), environmental ground water cleanup, and other surfactant based applications. In one aspect of the composition x is 0, 1, 2, 3, 4, 5, 6, 7, 8, 9, 10, 12, 14, 16, 18, 20, 21, 22, 23, 24, 25, 30, 35, 40, 45, and 50 and y is 0, 1, 2, 3, 4, 5, 6, 7, 8, 9, 10, 15, 20, 25, 30, 35, 40, 45, 50, 60, 70, 80, 90, and 100. In another aspect of the composition of the present invention if y is 0 then x is 1, 2, 3, 4, 5, 6, 7, 8, 9, 10, 12, 14, 16, 18, 20, 21, 22, 23, 24, 25, 30, 35, 40, 45 or 50 and if x is 0 then y is 1, 2, 3, 4, 5, 6, 7, 8, 9, 10, 15, 20, 25, 30, 35, 40, 45, 50, 60, 70, 80, 90 or 100. In a specific aspect the alkoxy sulfate surfactant has a formula $(C_6H_5CH_2CH_2)_3$—$C_6H_2O$—$PO_7$-$EO_{10}$—$SO_3^-$. In another aspect the alkoxy sulfate surfactant has a formula $(C_6H_5CH_2CH_2)_2$—$C_6H_3O$—$PO_7$-$EO_{10}$—$SO_3^-$.

In another embodiment the present invention also provides a method for making a alkoxy sulfate surfactant of formula (I) comprising the steps of:

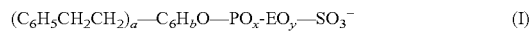

(i) alkoxylating a styrylphenol with a propylene oxide $(PO)_y$ group, an ethylene oxide $(EO)_z$ group or both in the presence of a basic catalyst, wherein a=3, b=2, a=2, b=3 or a=2-3, b=3-2, wherein x corresponds to the number of propoxy groups and ranges from 0 to 50, wherein y corresponds to the number of ethoxy groups and ranges from 0 to 100 and (ii) sulfating the alkoxylated styrylphenol by a sulfamic acid sulfation or any other mild sulfation process to make the styrylphenol alkoxy sulfate surfactant. In one aspect the styrylphenol alkoxy sulfate surfactant made by the method of the present invention is adapted for enhanced oil recovery (EOR), environmental ground water cleanup, and other surfactant based applications. In one aspect of the method x is 0, 1, 2, 3, 4, 5, 6, 7, 8, 9, 10, 12, 14, 16, 18, 20, 21, 22, 23, 24, 25, 30, 35, 40, 45, and 50 and y is 0, 1, 2, 3, 4, 5, 6, 7, 8, 9, 10, 15, 20, 25, 30, 35, 40, 45, 50, 60, 70, 80, 90, and 100. In another aspect of the method of the present invention if y is 0 then x is 1, 2, 3, 4, 5, 6, 7, 8, 9, 10, 12, 14, 16, 18, 20, 21, 22, 23, 24, 25, 30, 35, 40, 45 or 50 and if x is 0 then y is 1, 2, 3, 4, 5, 6, 7, 8, 9, 10, 15, 20, 25, 30, 35, 40, 45, 50, 60, 70, 80, 90 or 100.

In yet another aspect the basic catalyst is KOH, NaOH, NH$_4$OH, LiOH or any combinations thereof. In one aspect the styrylphenol alkoxy sulfate surfactant made by the method of the present invention comprises a counter-ion to a sulfate group, wherein the counter-ion is selected from the group consisting of Na, K, Mg, Ca, and NH$_4$. In a specific aspect the styrylphenol alkoxy sulfate surfactant has a formula $(C_6H_5CH_2CH_2)_3$—$C_6H_2O$—$PO_7$-$EO_{10}$—$SO_3^-$. In another aspect the alkoxy sulfate surfactant has a formula $(C_6H_5CH_2CH_2)_2$—$C_6H_3O$—$PO_7$-$EO_{10}$—$SO_3^-$.

One embodiment of the present invention is directed to a method of making a TSP alkoxy sulfate surfactant having a formula $(C_6H_5CH_2CH_2)_3$—$C_6H_2O$—$PO_7$-$EO_{10}$—$SO_3^-$ comprising the steps of: (i) propoxylating the TSP with propylene oxide (PO) in the presence of KOH or any other suitable basic catalyst to form a propoxylated TSP (TSP-7PO), wherein a mole ratio of the TSP:PO is 1:7, (ii) ethoxylating the propoxylated TSP with a ethylene oxide (EO) in the presence of KOH or any other suitable basic catalyst to form a TSP-7PO-10EO, wherein the mole ratio of the TSP-7PO:EO is 1:10, and (iii) sulfating the TSP-7PO-10EO by a sulfamic acid sulfation process to make the TSP alkoxy sulfate surfactant having the formula $(C_6H_5CH_2CH_2)_3$—$C_6H_2O$—$PO_7$-$EO_{10}$—$SO_3^-$. In one aspect the TSP alkoxy sulfate surfactant of formula $(C_6H_5CH_2CH_2)_3$—$C_6H_2O$—$PO_7$-$EO_{10}$—$SO_3^-$ is adapted for enhanced oil recovery (EOR), environmental ground water cleanup, and other surfactant based applications.

Another embodiment of the present invention discloses a composition for enhanced oil recovery (EOR), environmental ground water cleanup, and other surfactant based operations comprising: one or more alkoxy sulfate surfactants, wherein the one or more alkoxy sulfate surfactants have a general formula $(C_6H_5CH_2CH_2)_a$—$C_6H_bO$—$PO_x$-$EO_y$—$SO_3^-M^+$, wherein a=3, b=2, a=2, b=3 or a=2-3, b=3-2, wherein x corresponds to the number of propoxy groups and ranges from 0 to 50, wherein y corresponds to the number of ethoxy groups and ranges from 0 to 100, wherein M is a counter ion to a sulfate group, wherein M is selected from the group consisting of Na, K, Mg, Ca, and NH$_4$, one or more alkalinity generating agents, and a solvent, wherein the one or more styrylphenol alkoxy sulfate surfactants, the one or more alkalinity generating agents are dissolved in the solvent.

In one aspect the one or more alkalinity generating agents comprise alkali earth metal hydroxides, NaOH, KOH, LiOH, NH$_4$OH, Na$_2$CO$_3$, NaHCO$_3$, Na-metaborate, sodium silicate, sodium orthosilicate, EDTANa$_4$, other polycarboxylates or any combinations thereof. In another aspect the solvent comprises water, hard brine, hard water, polymer containing solutions, gas foam or any combinations thereof. In yet another aspect, the composition is adapted for use alone, in an alkaline-surfactant-polymer formulation or in a gas foam for EOR applications. In one aspect the composition contains 0.1%, 0.5%, 1% 2%, 3%, 4%, and 5% of the one or more alkalinity generating agents. In another aspect of the composition x is 0, 1, 2, 3, 4, 5, 6, 7, 8, 9, 10, 12, 14, 16, 18, 20, 21, 22, 23, 24, 25, 30, 35, 40, 45, and 50 and y is 0, 1, 2, 3, 4, 5, 6, 7, 8, 9, 10, 15, 20, 25, 30, 35, 40, 45, 50, 60, 70, 80, 90, and 100. In yet another aspect of the composition of the present invention if y is 0 then x is 1, 2, 3, 4, 5, 6, 7, 8, 9, 10, 12, 14, 16, 18, 20, 21, 22, 23, 24, 25, 30, 35, 40, 45 or 50 and if x is 0 then y is 1, 2, 3, 4, 5, 6, 7, 8, 9, 10, 15, 20, 25, 30, 35, 40, 45, 50, 60, 70, 80, 90 or 100. In another aspect, the composition is adapted for EOR from a crude oil, wherein the crude oil comprises paraffin based crude oils, asphaltene based crude oils or combinations and mixtures thereof. In yet another aspect the composition is adapted for EOR from an asphaltene based crude oil. In a specific aspect, the alkoxy sulfate surfactant has a formula $(C_6H_5CH_2CH_2)_3$—$C_6H_2O$—$PO_7$-$EO_{10}$—$SO_3^-$. In another aspect the alkoxy sulfate surfactant has a formula $(C_6H_5CH_2CH_2)_2$—$C_6H_3O$—$PO_7$-$EO_{10}$—$SO_3^-$.

In yet another embodiment, the present invention describes a method of enhanced oil recovery (EOR) from a hydrocarbon bearing formation comprising the steps of: injecting an alkoxy sulfate surfactant composition having a general formula $(C_6H_5CH_2CH_2)_a$—$C_6H_bO$—$PO_x$-$EO_y$—$SO_3^-M^+$, wherein a=3, b=2, a=2, b=3 or a=2-3, b=3-2, wherein x corresponds to the number of propoxy groups and ranges from 0 to 50, wherein y corresponds to the number of ethoxy groups and ranges from 0 to 100, wherein M is a counter ion to a sulfate group, wherein M is selected from the group consisting of Na, K, Mg, Ca, and NH$_4$, alone, as an alkaline-surfactant-polymer formulation (ASP) or a gas foam into the hydrocarbon bearing formation at a temperature from 25 to 120° C., wherein the styrylphenol alkoxy sulfate surfactant composition is in water, hard water or hard brine and comprises greater that 0.05% of one or more alkalinity generating agents and injecting a polymer "push" solution or the gas foam to recover the oil.

In one aspect of the EOR method of the present invention, the one or more alkalinity generating agents comprise alkali earth metal hydroxides, NaOH, KOH, LiOH, NH4OH, Na$_2$CO$_3$, NaHCO$_3$, Na-metaborate, sodium silicate, sodium orthosilicate, EDTANa$_4$, other polycarboxylates or any combinations thereof. In another aspect of the method x is 0, 1, 2, 3, 4, 5, 6, 7, 8, 9, 10, 12, 14, 16, 18, 20, 21, 22, 23, 24, 25, 30, 35, 40, 45, and 50 and y is 0, 1, 2, 3, 4, 5, 6, 7, 8, 9, 10, 15, 20, 25, 30, 35, 40, 45, 50, 60, 70, 80, 90, and 100. In yet another aspect of the method of the present invention if y is 0 then x is 1, 2, 3, 4, 5, 6, 7, 8, 9, 10, 12, 14, 16, 18, 20, 21, 22, 23, 24, 25, 30, 35, 40, 45 or 50 and if x is 0 then y is 1, 2, 3, 4, 5, 6, 7, 8, 9, 10, 15, 20, 25, 30, 35, 40, 45, 50, 60, 70, 80, 90 or 100. In yet another aspect, the hydrocarbon bearing formation comprises one or more paraffin based crude oils, asphaltene based crude oils or combinations and mixtures thereof. In another aspect the hydrocarbon bearing formation comprises an asphaltene based crude oil. In a specific aspect of the EOR method of the present invention the styrylphenol alkoxy sulfate surfactant has a formula $(C_6H_5CH_2CH_2)_3$—$C_6H_2O$—$PO_7$-$EO_{10}$—$SO_3^-$. In another aspect the alkoxy sulfate surfactant has a formula $(C_6H_5CH_2CH_2)_2$—$C_6H_3O$—$PO_7$-$EO_{10}$—$SO_3^-$.

The present invention in one embodiment discloses a composition and a method of manufacture of a high molecular weight non-ionic surfactant composition of formula (II) comprising an alkoxy group, wherein the alkoxy groups are selected from the group consisting of a poly propoxy (PO) and a poly ethoxy (EO) group

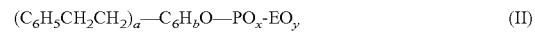

$$(C_6H_5CH_2CH_2)_a\text{—}C_6H_bO\text{—}PO_x\text{-}EO_y \tag{II}$$

wherein a=3, b=2, a=2, b=3 or a=2-3, b=3-2, wherein, x corresponds to the number of propoxy groups and ranges from 0 to 50 and y corresponds to the number of ethoxy groups and ranges from 0 to 100. In one aspect, the composition is adapted for enhanced oil recovery (EOR), environmental ground water cleanup, and other surfactant based applications. The present invention also discloses a method for making a high molecular weight non-ionic surfactant of formula (II) comprising a styrylphenol alkoxy group, wherein the alkoxy groups are selected from the group consisting of a poly propoxy (PO) and a poly ethoxy (EO) group comprising the step of:

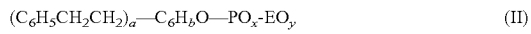  (II)

alkoxylating the styrylphenol with a propylene oxide $(PO)_y$ group, an ethylene oxide $(EO)_z$ group or both in the presence of a basic catalyst, wherein x corresponds to the number of propoxy groups and ranges from 0 to 50 and y corresponds to the number of ethoxy groups and ranges from 0 to 100. In one aspect of the method, the high molecular weight non-ionic surfactant is adapted for enhanced oil recovery (EOR), environmental ground water cleanup, and other surfactant based applications.

Another embodiment of the present invention relates to a method of recovering an asphaltene based crude oil from a hydrocarbon bearing formation comprising the steps of: injecting an alkoxy sulfate surfactant composition having a general formula $(C_6H_5CH_2CH_2)_a$—$C_6H_bO$—$PO_x$-$EO_y$—$SO_3^-M^+$, wherein a=3, b=2, a=2, b=3 or a=2-3, b=3-2, wherein x corresponds to the number of propoxy groups and ranges from 0 to 50, wherein y corresponds to the number of ethoxy groups and ranges from 0 to 100, wherein M is a counter ion to a sulfate group, wherein M is selected from the group consisting of Na, K, Mg, Ca, and $NH_4$, alone, as an alkaline-surfactant-polymer formulation (ASP) or in a gas foam into the hydrocarbon bearing formation at a temperature from 25 to 120° C., wherein the alkoxy sulfate surfactant composition is in water, hard water or hard brine and comprises greater that 0.05% of one or more alkalinity generating agents and injecting a polymer "push" solution or the gas foam to recover the oil. In one aspect, the one or more alkalinity generating agents comprise alkali earth metal hydroxides, NaOH, KOH, LiOH, $NH_4OH$, $Na_2CO_3$, $NaHCO_3$, Na-metaborate, sodium silicate, sodium orthosilicate, $EDTANa_4$, other polycarboxylates or any combinations thereof. In another aspect x is 0, 1, 2, 3, 4, 5, 6, 7, 8, 9, 10, 12, 14, 16, 18, 20, 21, 22, 23, 24, 25, 30, 35, 40, 45, and 50. In another aspect y is 0 and x is 1, 2, 3, 4, 5, 6, 7, 8, 9, 10, 12, 14, 16, 18, 20, 21, 22, 23, 24, 25, 30, 35, 40, 45 or 50. In another aspect y is 0, 1, 2, 3, 4, 5, 6, 7, 8, 9, 10, 15, 20, 25, 30, 35, 40, 45, 50, 60, 70, 80, 90, and 100. In another aspect x is 0 and y is 1, 2, 3, 4, 5, 6, 7, 8, 9, 10, 15, 20, 25, 30, 35, 40, 45, 50, 60, 70, 80, 90 or 100. In yet another aspect the styrylphenol alkoxy sulfate surfactant has a formula $(C_6H_5CH_2CH_2)_3$—$C_6H_2O$—$PO_7$-$EO_{10}$—$SO_3^-$. In another aspect the alkoxy sulfate surfactant has a formula $(C_6H_5CH_2CH_2)_2$—$C_6H_3O$—$PO_7$-$EO_{10}$—$SO_3^-$.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
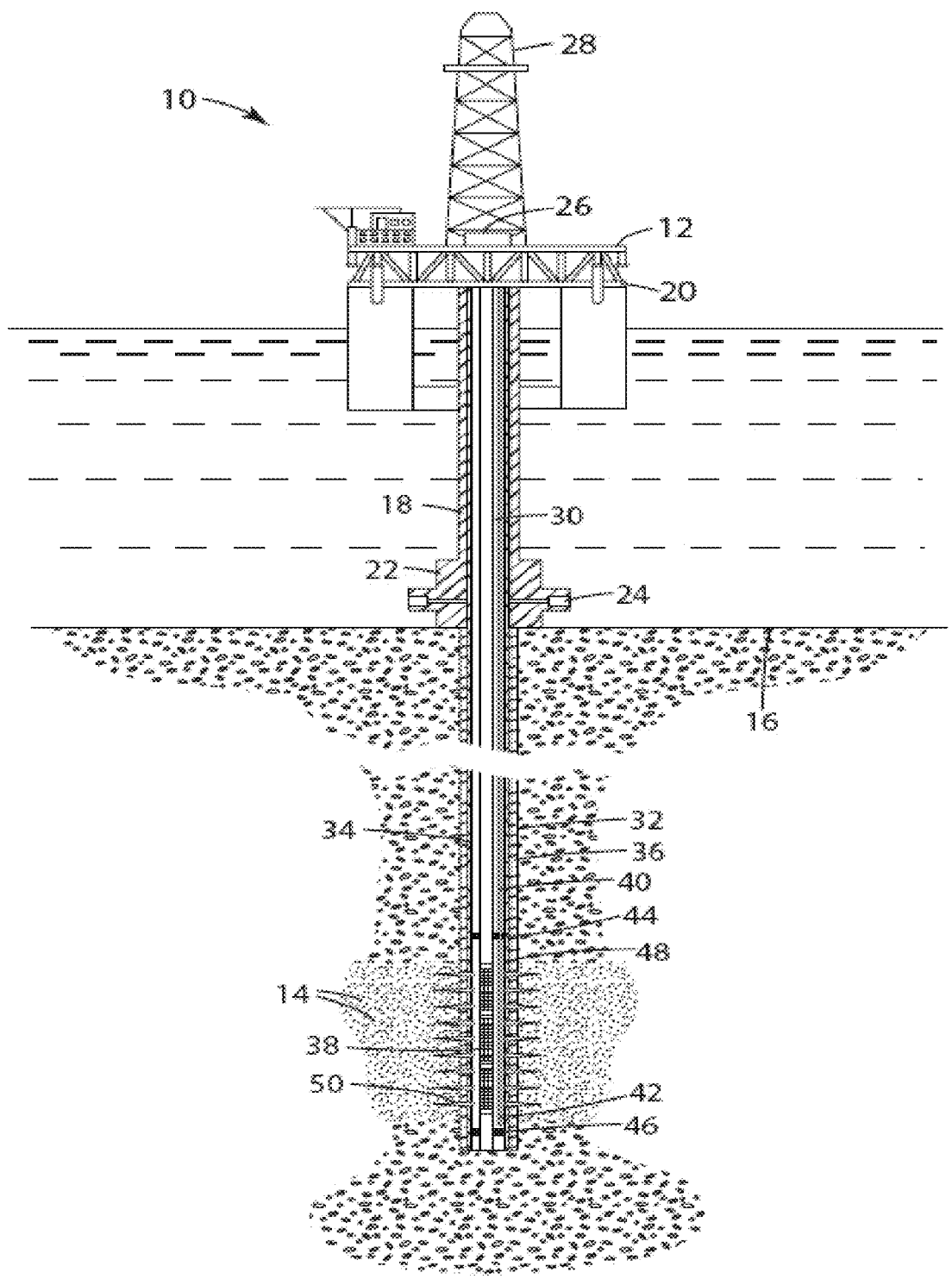
FIG. 1 is a schematic illustration of an offshore oil platform with facilities for injecting chemical solutions into the reservoir for the purpose of flooding the reservoir to enhance the oil recovery according to some embodiments of the present invention.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present invention describes a novel surfactant composition for enhanced oil recovery (EOR) applications. The composition described herein is a tristyrylphenol (TSP) alkoxylate. TSP is a commercially available large hydrophobe. Although this is a sterically bulky molecule, it is a phenol and as such is easily amenable to alkoxylation with alkylene oxides such as propylene oxide (PO), ethylene oxide (EO) or both. After alkoxylation, the TSP alkoxylate is sulfated to produce a highly effective and efficient anionic surfactant for EOR applications.

The present inventors tested a surfactant in the form of TSP-7PO-10EO-Sulfate. The findings of studies by the present inventors indicated that it was an excellent surfactant for solubilizing crude oil in Brine. The TSP alkoxylate surfactants of the present invention have a great affinity to the asphaltene containing crude oils due to the high aromatic nature of the surfactant hydrophobe, thus enabling an enhanced recovery of the asphaltene based crudes from a hydrocarbon bearing formation.

The general structure of the styrylphenol alkoxylate sulfate surfactants of the present invention is as follows:

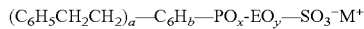

wherein a=3, b=2, a=2, b=3 or a=2-3, b=3-2, x corresponds to the number of propoxy groups and ranges from 0 to 50, and y corresponds to the number of ethoxy groups and ranges from 0 to 100. It will be understood herein that a=2-3 is indicative of an average of between 2 and 3 styryl groups per phenol molecule. Taking into account the process utilized in commercial production of styryl phenols which involves acid catalyzed alkylation of phenol with styrene, this average may be achieved by any combination of distyryl phenol and tristyryl phenol along with any residual monostyryl phenol. For example a=2.1 represents a composition comprising 90% distyryl phenol and 10% TSP, a=2.6 represents a composition comprising 40% distyryl phenol and 60% TSP, a=2.9 represents a composition comprising 10% distyryl phenol and 90% TSP and other combinations thereof.

The present invention also provides compositions of styrylphenol alkoxylate surfactants that comprise only a distyryl phenol (100%), only a TSP (100%) or mixtures having different ratios of the di- and tristyryl phenols (for e.g.

90:10, 80:20, 70:30, 60:40, 50:50, 40:60, 30:70, 20:80, 10:90, 75:25, 63:37, 55:45, 42:58, 28:72, 12:88, 5:95, and any other combinations thereof).

The general structure of the TSP-7PO-10EO-Sulfate is as follows:

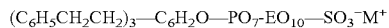

(C$_6$H$_5$CH$_2$CH$_2$)$_3$—C$_6$H$_2$O—PO$_7$-EO$_{10}$—SO$_3^-$M$^+$ where, M is the counter ion of the sulfate (Na, K, Ca, Mg, NH$_4$). The molecules described hereinabove have applications in alkaline-surfactant-polymer formulation (ASP) or in a gas foam formulation for EOR.

The novelty of the TSP alkoxylate sulfate surfactants of the present invention arises from the four phenyl groups as part of the polyaromatic hydrophobe, its size which can be further enhanced by the addition of alkylene oxides such as PO. The large hydrophobicity is balanced by an equally large EO block in combination with anionic sulfate group to reach a desired hydrophilic-lipophilic balance (HLB) for the surfactant. Furthermore, the unsulfated versions of the large hydrophobe alkoxylated TSP of the present invention can be used as ultra-high molecular weight non-ionic surfactants Normally, large hydrophobe anionics are inherently less soluble in aqueous medium necessitating the use of co-solvents which in turn increases the optimal salinity. This issue is addressed by molecules such as the TSP alkoxy sulfates of the present invention that have good aqueous solubility while maintaining high surface activity. Thus, the need for a co-solvent is obviated or minimized for improving the water solubility of the surfactant formulation. A co-solvent, if used, may serve other purposes such as improvement of the viscosity of the middle phases, promoting faster equilibration, etc.

Sulfation of a hydrophobe is the simplest and most versatile method of making anionic surfactants. Consequently, a new array of anionic surfactants that can find applications in high temperature reservoir EOR applications becomes available. Sulfation, by virtue of its simplicity, is the least expensive method of incorporating anionic functionality in a surfactant.

The present invention can be used in any application (e.g., surface or near-surface treatments, down hole or for Enhanced Oil Recovery) that involves low to high temperature conditions, such as, environmental clean up of ground water contaminated by oils and other organic solvents. In addition, the TSP-alkoxylate sulfate is applicable to cleaning and aquifer remediation work. The unsulfated alkoxylate sulfate is an attractive non-ionic surfactant in its own right. In addition to the sulfate, the alkoxylate can be transformed into chemically stable sulfonates, glyceryl sulfonates, etc.

The synthesis sequence of TSP-7PO-10EO-Sulfate comprises the standard propoxylation-ethoxylation processes at ~125° C. on TSP using KOH catalysis, followed by standard Sulfamic acid sulfation at ~80° C.

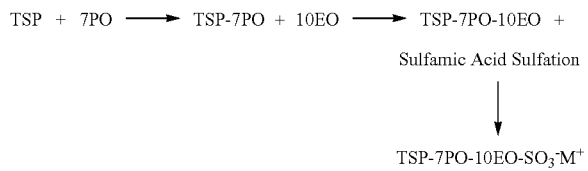

TSP + 7PO ⟶ TSP-7PO + 10EO ⟶ TSP-7PO-10EO +

Sulfamic Acid Sulfation

↓

TSP-7PO-10EO-SO$_3^-$M$^+$

The following definitions of terms apply throughout the specification and claims.

For methods of treating a hydrocarbon-bearing formation and/or a well bore, the term "treating" includes placing a chemical (e.g., a fluorochemical, cationic polymer, or corrosion inhibitor) within a hydrocarbon-bearing formation using any suitable manner known in the art (e.g., pumping, injecting, pouring, releasing, displacing, spotting, or circulating the chemical into a well, well bore, or hydrocarbon-bearing formation).

The term "crude oil" as used herein encompasses oleaginous materials such as those found in the oil field deposits, oil shales, tar sands, heavy oil deposits, and the like. "Crude oils" generally refer to a mixture of naturally occurring hydrocarbons that is refined into diesel, gasoline, heating oil, jet fuel, kerosene, and literally thousands of other products called petrochemicals. Crude oils are named according to their contents and origins, and classified according to their per unit weight (specific gravity). Heavier crudes yield more heat upon burning, but have lower API gravity and market price in comparison to light (or sweet) crudes.

"Crude oils" vary widely in appearance and viscosity from field to field. They range in color, odor, and in the properties they contain. While all crude oils are essentially hydrocarbons, the differences in properties, especially the variations in molecular structure, determine whether a "crude oil" is more or less easy to produce, pipeline, and refine. The variations may even influence its suitability for certain products and the quality of those products. "Crude oils" are roughly classified into three groups, according to the nature of the hydrocarbons they contain. (i) Paraffin based crude oils: these contain higher molecular weight paraffins which are solid at room temperature, but little or no asphaltic (bituminous) matter. They can produce high-grade lubricating oils, (ii) Asphaltene based crude oils: these contain large proportions of asphaltic matter, and little or no paraffin. Some are predominantly naphthenes and so yield lubricating oils that are more sensitive to temperature changes than the paraffin-based crudes, and (iii) Mixed based crude oils: these contain both paraffins and naphthenes, as well as aromatic hydrocarbons. Most crudes fit this category.

The term "polymer" refers to a molecule having a structure that essentially includes the multiple repetitions of units derived, actually or conceptually, from molecules of low relative molecular mass. The term "polymer" includes "oligomer".

The term "bonded" refers to having at least one of covalent bonding, hydrogen bonding, ionic bonding, Van Der Waals interactions, pi interactions, London forces, or electrostatic interactions.

The term "productivity" as applied to a well refers to the capacity of a well to produce hydrocarbons; that is, the ratio of the hydrocarbon flow rate to the pressure drop, where the pressure drop is the difference between the average reservoir pressure and the flowing bottom hole well pressure (i.e., flow per unit of driving force). This term is not pertinent to enhanced oil recovery. It applies to near wellbore treatments such as the 3M treatment, but here the idea is to flood the entire reservoir with chemical solutions to mobilize and displace the oil to the production wells.

"Alkyl group" and the prefix "alk-" are inclusive of both straight chain and branched chain groups and of cyclic groups having up to 30 carbons (in some embodiments, up to 20, 15, 12, 10, 8, 7, 6, or 5 carbons) unless otherwise specified. Cyclic groups can be monocyclic or polycyclic and, in some embodiments, have from 3 to 10 ring carbon atoms.

"Alkylene" is the divalent form of the "alkyl" groups defined above.

"Arylalkylene" refers to an "alkylene" moiety to which an aryl group is attached.

The term "aryl" as used herein includes carbocyclic aromatic rings or ring systems, for example, having 1, 2, or 3 rings and optionally containing at least one heteroatom (e.g., O, S, or N) in the ring. Examples of aryl groups include phenyl, naphthyl, biphenyl, fluorenyl as well as furyl, thienyl, pyridyl, quinolinyl, isoquinolinyl, indolyl, isoindolyl, triazolyl, pyrrolyl, tetrazolyl, imidazolyl, pyrazolyl, oxazolyl, and thiazolyl.

"Arylene" is the divalent form of the "aryl" groups defined above.

Referring to FIG. 1, an exemplary offshore oil platform is schematically illustrated and generally designated 10. Semi-submersible platform 12 is centered over submerged hydrocarbon-bearing formation 14 located below sea floor 16. Sub-sea conduit 18 extends from deck 20 of platform 12 to wellhead installation 22 including blowout preventers 24. Platform 12 is shown with hoisting apparatus 26 and derrick 28 for raising and lowering pipe strings such as work string 30.

Wellbore 32 extends through the various earth strata including hydrocarbon-bearing formation 14. Casing 34 is cemented within wellbore 32 by cement 36. Work string 30 may include various tools including, for example, sand control screen assembly 38 which is positioned within wellbore 32 adjacent to hydrocarbon-bearing formation 14. Also extending from platform 12 through wellbore 32 is fluid delivery tube 40 having fluid or gas discharge section 42 positioned adjacent to hydrocarbon-bearing formation 14, shown with production zone 48 between packers 44, 46. When it is desired to treat the near-wellbore region of hydrocarbon-bearing formation 14 adjacent to production zone 48, work string 30 and fluid delivery tube 40 are lowered through casing 34 until sand control screen assembly 38 and fluid discharge section 42 are positioned adjacent to the near-wellbore region of hydrocarbon-bearing formation 14 including perforations 50. Thereafter, a composition described herein is pumped down delivery tube 40 to progressively treat the near-wellbore region of hydrocarbon-bearing formation 14.

Phase Behavior Procedures

Phase Behavior Screening: Phase behavior experiments have been used to characterize chemicals for EOR. There are many benefits in using phase behavior as a screening method. Phase Behavior studies are used to determine: (1) the effect of electrolytes; (2) oil solubilization, IFT reduction, (3) microemulsion densities; (4) surfactant and microemulsion viscosities; (5) coalescence times; (6) identify optimal surfactant-cosolvent formulations; and/or (7) identify optimal formulation for coreflood studies.

Thermodynamically stable phase can form with oil, water and surfactant mixtures. Surfactants form micellar structures at concentrations above the critical micelle concentration (CMC). The emulsion coalesces into a separate phase at the oil-water interface and is referred to as a microemulsion. A microemulsion is a surfactant-rich distinct phase consisting of surfactant, oil and water and possibly co-solvents and other components. This phase is thermodynamically stable in the sense that it will return to the same phase volume at a given temperature. Some workers in the past have added additional requirements, but for the purposes of this engineering study, the only requirement will be that the microemulsion is a thermodynamically stable phase.

The phase transition is examined by keeping all variables fixed except for the scanning variable. The scan variable is changed over a series of pipettes and may include, but is not limited to, salinity, temperature, chemical (surfactant, alcohol, electrolyte), oil, which is sometimes characterized by its equivalent alkane carbon number (EACN), and surfactant structure, which is sometimes characterized by its hydrophilic-lipophilic balance (HLB). The phase transition was first characterized by Winsor (1954) into three regions: Type I—excess oleic phase, Type III—aqueous, microemulsion and oleic phases, and the Type II—excess aqueous phase. The phase transition boundaries and some common terminology are described as follows: Type I to III—lower critical salinity, Type III to II—upper critical salinity, oil solubilization ratio (Vo/Vs), water solubilization ratio (Vw/Vs), the solubilization value where the oil and water solubilization ratios are equal is called the Optimum Solubilization Ratio ($\sigma^*$), and the electrolyte concentration where the optimum solubilization ratio occurs is referred to as the Optimal Salinity (S*).

Determining Interfacial Tension: Efficient use of time and lab resources can lead to valuable results when conducting phase behavior scans. A correlation between oil and water solubilization ratios and interfacial tension was suggested by Healy and Reed (1976) and a theoretical relationship was later derived by Chun Huh (1979). Lowest oil-water IFT occurs at optimum solubilization as shown by the Chun Huh theory. This is equated to an interfacial tension through the Chun Huh equation, where IFT varies with the inverse square of the solubilization ratio:

$$\gamma = \frac{C}{\sigma^2} \tag{1}$$

For most crude oils and microemulsions, C=0.3 is a good approximation. Therefore, a quick and convenient way to estimate IFT is to measure phase behavior and use the Chun-Huh equation to calculate IFT. The IFT between microemulsions and water and/or oil can be very difficult and time consuming to measure and is subject to larger errors, so using the phase behavior approach to screen hundreds of combinations of surfactants, co-surfactants, co-solvents, electrolytes, oil, and so forth is not only simpler and faster, but avoids the measurement problems and errors associated with measuring IFT especially of combinations that show complex behavior (gels and so forth) and will be screened out anyway. Once a good formulation has been identified, then it is still a good idea to measure IFT.

Equipment: Phase behavior experiments are created with the following materials and equipment.

Mass Balance: Mass balances are used to measure chemicals for mixtures and determine initial saturation values of cores.

Water Deionizer: Deionized (DI) water is prepared for use with all the experimental solutions using a Nanopure™ filter system. This filter uses a recirculation pump and monitors the water resistivity to indicate when the ions have been removed. Water is passed through a 0.45 micron filter to eliminate undesired particles and microorganisms prior to use.

Borosilicate Pipettes: Standard 5 mL borosilicate pipettes with 0.1 mL markings are used to create phase behavior scans as well as run dilution experiments with aqueous solutions. Ends are sealed using a propane and oxygen flame.

Pipette Repeater: An Eppendorf Repeater Plus® instrument is used for most of the pipetting. This is a handheld dispenser calibrated to deliver between 25 microliter and 1 ml increments. Disposable tips are used to avoid contamination between stocks and allow for ease of operation and consistency.

Propane-Oxygen Torch: A mixture of propane and oxygen gas is directed through a Bernz-O-Matic flame nozzle to create a hot flame about ½ inch long. This torch is used to flame-seal the glass pipettes used in phase behavior experiments.

Convection Ovens: Several convection ovens are used to incubate the phase behaviors and core flood experiments at the reservoir temperatures. The phase behavior pipettes are primarily kept in Blue M and Memmert ovens that are monitored with mercury thermometers and oven temperature gauges to ensure temperature fluctuations are kept at a minimal between recordings. A large custom built flow oven was used to house most of the core flood experiments and enabled fluid injection and collection to be done at reservoir temperature.

pH Meter: An ORION research model 701/digital ion analyzer with a pH electrode is used to measure the pH of most aqueous samples to obtain more accurate readings. This is calibrated with 4.0, 7.0 and 10.0 pH solutions. For rough measurements of pH, indicator papers are used with several drops of the sampled fluid.

Phase Behavior Calculations: The oil and water solubilization ratios are calculated from interface measurements taken from phase behavior pipettes. These interfaces are recorded over time as the mixtures approached equilibrium and the volume of any macroemulsions that initially formed decreased or disappeared. The procedure for creating phase behavior experiments will be discussed later.

Oil Solubilization Ratio: The oil solubilization ratio is defined as the volume of oil solubilized divided by the volume of surfactant in microemulsion. All the surfactant is presumed to be in the emulsion phase. The oil solubilization ratio is applied for Winsor type I and type III behavior. The volume of oil solubilized is found by reading the change between initial aqueous level and excess oil (top) interface level. The oil solubilization parameter is calculated as follows:

$$\sigma_o = \frac{V_o}{V_s} \quad (2)$$

$\sigma_o$=oil solubilization ratio
$V_o$=volume of oil solubilized
$V_s$=volume of surfactant Water Solubilization Ratio: The water solubilization ratio is defined as the volume of water solubilized divided by the volume of surfactant in microemulsion. All the surfactant is presumed to be in the emulsion phase. The water solubilization ratio is applied for Winsor type III and type II behavior. The volume of water solubilized is found by reading the change between initial aqueous level and excess water (bottom) interface level. The water solubilization parameter is calculated as follows:

$$\sigma_w = \frac{V_w}{V_s} \quad (3)$$

$\sigma_w$=water solubilization ratio
$V_w$=volume of water solubilized

Optimum Solubilization Ratio: The optimum solubilization ratio occurs where the oil and water solubilization is equal. The coarse nature of phase behavior screening often does not include a data point at optimum, so the solubilization curves are drawn for the oil and water solubilization and the intersection of these two curves is defined as the optimum. The following is true for the optimum solubilization ratio:

$$\sigma_o = \sigma_w = \sigma^* \quad (4)$$

$\sigma^*$=optimum solubilization parameter

Phase Behavior Methodology: The methods for creating, measuring and recording observations are described in this section. Scans are made using a variety of electrolyte mixtures described below. Oil is added to most aqueous surfactant solutions to see if a microemulsion formed, how long it took to form and equilibrate if it formed, what type of microemulsion formed and some of its properties such as viscosity. However, the behavior of aqueous mixtures without oil added is also important and is also done in some cases to determine if the aqueous solution is clear and stable over time, becomes cloudy or separated into more than one phase.

Preparation of Samples: Phase Behavior Samples are Made by First Preparing Surfactant stock solutions and combining them with brine stock solutions in order to observe the behavior of the mixtures over a range of salinities. All the experiments are created at or above 0.1 wt % active surfactant concentration, which is above the typical CMC of the surfactant.

Solution Preparation: Surfactant stocks are based on active weight-percent surfactant (and co-surfactant when incorporated). The masses of surfactant, co-surfactant, co-solvent and de-ionized water (DI) are measured out on a balance and mixed in glass jars using magnetic stir bars. The order of addition is recorded on a mixing sheet along with actual masses added and the pH of the final solution. Brine solutions are created at the necessary weight percent concentrations for making the scans.

Surfactant Stock: The chemicals being tested are first mixed in a concentrated stock solution that usually consisted of a primary surfactant, co-solvent and/or co-surfactant along with de-ionized water. The quantity of chemical added is calculated based on activity and measured by weight percent of total solution. Initial experiments are at about 1-3% active surfactant so that the volume of the middle microemulsion phase would be large enough for accurate measurements assuming a solubilization ratio of at least 10 at optimum salinity.

Polymer Stock: Often these stocks were quite viscous and made pipetting difficult so they are diluted with de-ionized water accordingly to improve ease of handling. Mixtures with polymer are made only for those surfactant formulations that showed good behavior and merited additional study for possible testing in core floods. Consequently, scans including polymer are limited since they are done only as a final evaluation of compatibility with the surfactant.

Pipetting Procedure: Phase behavior components are added volumetrically into 5 ml pipettes using an Eppendorf Repeater Plus or similar pipetting instrument. Surfactant and brine stocks are mixed with DI water into labeled pipettes and brought to temperature before agitation. Almost all of the phase behavior experiments are initially created with a water oil ratio (WOR) of 1:1, which involved mixing 2 ml of the aqueous phase with 2 ml of the evaluated crude oil or hydrocarbon, and different WOR experiments are mixed accordingly. The typical phase behavior scan consisted of 10-20 pipettes, each pipette being recognized as a data point in the series.

Order of Addition: Consideration had to be given to the addition of the components since the concentrations are often several fold greater than the final concentration. Therefore, an order is established to prevent any adverse effects resulting from surfactant or polymer coming into direct contact with the concentrated electrolytes. The desired sample compositions are made by combining the stocks in the following order: (1) Electrolyte stock(s); (2) De-ionized water; (3) Surfactant stock; (4) Polymer stock; and (5) Crude oil or hydrocarbon. Any air bubbles trapped in the bottom of the pipettes are tapped out (prior to the addition of surfactant to avoid bubbles from forming).

Initial Observations: Once the components are added to the pipettes, sufficient time is allotted to allow all the fluid to drain down the sides. Then aqueous fluid levels are recorded before the addition of oil. These measurements are marked on record sheets. Levels and interfaces are recorded on these documents with comments over several days and additional sheets are printed as necessary.

Sealing and Mixing: The pipettes are blanketed with argon gas to prevent the ignition of any volatile gas present by the flame sealing procedure. The tubes are then sealed with the propane-oxygen torch to prevent loss of additional volatiles when placed in the oven. Pipettes are arranged on the racks to coincide with the change in the scan variable. Once the phase behavior scan is given sufficient time to reach reservoir temperature (15-30 minutes), the pipettes are inverted several times provide adequate mixing. Tubes are observed for low tension upon mixing by looking at droplet size and how uniform the mixture appeared. Then the solutions are allowed to equilibrate over time and interface levels are recorded to determine equilibration time and surfactant performance.

Measurements and Observations: Phase behavior experiments are allowed to equilibrate in oven that is set to the reservoir temperature for the crude oil being tested. The fluid levels in the pipettes are recorded periodically and the trend in the phase behavior observed over time. Equilibrium behavior is assumed when fluid levels ceased to change within the margin of error for reading the samples.

Fluid Interfaces: The fluid interfaces are the most crucial element of phase behavior experiments. From them, the phase volumes are determined and the solubilization ratios are calculated. The top and bottom interfaces are recorded as the scan transitioned from an oil-in-water microemulsion to a water-in-oil microemulsion. Initial readings are taken one day after initial agitation and sometimes within hours of agitation if coalescence appeared to happen rapidly. Measurements are taken thereafter at increasing time intervals (for example, one day, four days, one week, two weeks, one month and so on) until equilibrium is reached or the experiment is deemed unessential or uninteresting for continued observation.

Figure 2:
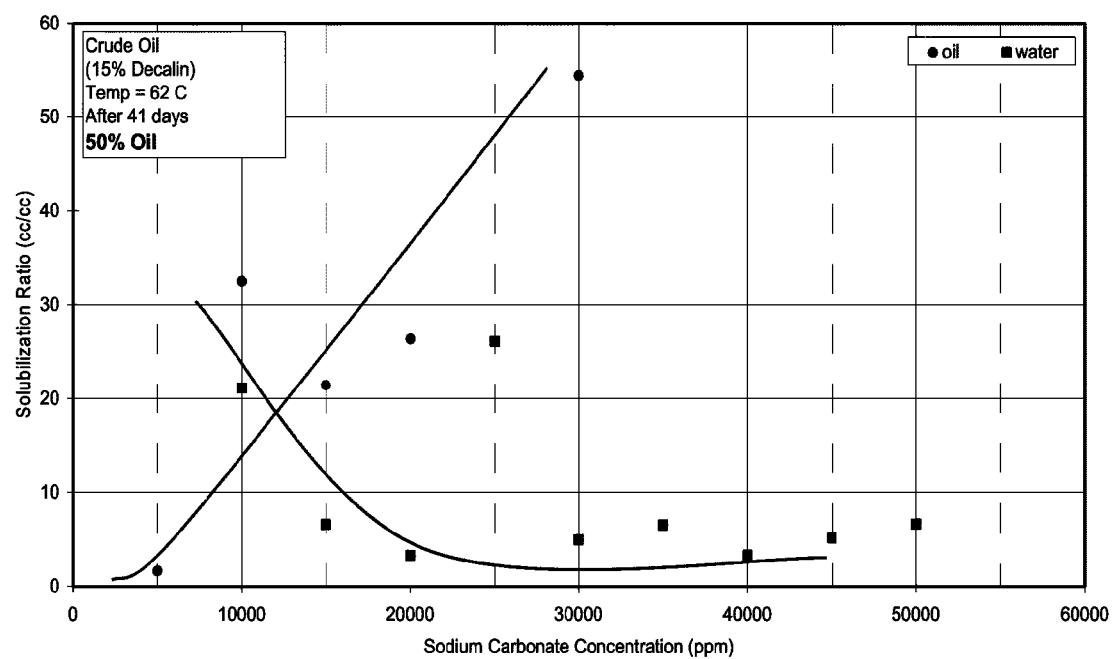
FIG. 2 is a solubilization plot for the system comprising 0.15% $C_{20-24}$ IOS, 0.15% TSP-7PO-10EO Sulfate, 0.15% 4-methyl-2-pentanol.

Table 1 shows phase behavior data recording sheets corresponding to plot shown in FIG. 2 for the system comprising 0.15% C2024 IOS, 0.15% TSP-7PO-10EO Sulfate, 0.15% 4-methyl-2-pentanol. As seen from the plots the optimum solubilization ratio for the case is around 19 cc/cc (FIG. 2). The IFT calculated from Chun-Huh's formula as previously described is:

$$\sigma = V_o V_s (cc/cc)$$
$$= 0.3/19^2$$
$$= 8.3102 \times 10^{-4} \text{ dynes/cm}$$

In general, a solubilization ratio of 10 cc/cc or higher is regarded as reflecting a system with ultra-low IFT.

TABLE 1

Phase behavior data recording sheet.

| Experiment | crude #8 +15.2% decalin | | 0.15% 2024 IOS, 0.15% TSP-7PO-10 SO4, 0.15% 4-methyl-2-pentanol | | |
|---|---|---|---|---|---|
| Hydrocarbon | | | Hydrocarbon Density | 0 g/cc | Typical hydrocarbon Densities: |
| Surfactant | C20-24 IOS | | Total Surfactant Conc. | 0.3 wt % | Octane |
| Co-Surfactant (1) | TSP-7PO-10 SO4 | | Total Alcohol Conc. | 0.15 wt % | Decane |
| Co-Solvent | 4-methyl-2-penanol | | Polymer Conc. | 0 wt % | |
| Surfactant Conc. | 0.15 wt % | | Na2CO3 Conc. | 0.15 wt % | |
| Co-surf (1) Conc. | 0.15 wt % | | WOR | 1 | Mixed: Dec. 10, 2009 |
| cosolvent Conc. | wt % | | Temperature | 62 Celcius | |
| MA8OI Conc. | | | Tube Size | 5 mL | |
| NaCl:CaCl Ratio | | | | | |

| Salinity (wt % Na2CO3) | (ppm Na2CO3) | Hydrocarbon Level | Aqueous Level | Top of emulsion | Top Interface | Bottom Interface | Bottom of emulsion | Type | Volume of Oil Solubilized (cc) | Volume of Water Solubilized (cc) | Oil Sol. Ratio (cc/cc) | Water Sol. Ratio (cc/cc) | HC Sol. (mg/L) | Volume Fraction of Oil ($V_o$) | Volume Fraction of Microemulsion ($V_{me}$) | Volumn Fraction of Water ($V_w$) | $V_w + V_{me}$ | Notes |
|---|---|---|---|---|---|---|---|---|---|---|---|---|---|---|---|---|---|---|
| Reading: | | 41 days | Jan. 20, 2010 | | | | | | | | | | | | | | | Extended scan |
| 0.50% | 5000 | | 2.99 | | 2.98 | 3.08 | | I | 0.01 | | 1.7 | | 0 | 0.596 | 0.404 | 0.000 | 0.404 | |
| 1.00% | 10000 | | 2.95 | | 2.75 | 3.02 | | III | 0.20 | 0.13 | 32.5 | 21.1 | 0 | 0.550 | 0.066 | 0.384 | 0.450 | |
| 1.50% | 15000 | | 2.98 | | 2.85 | 3.00 | | III | 0.13 | 0.04 | 21.5 | 6.6 | 0 | 0.570 | 0.034 | 0.396 | 0.430 | |
| 2.00% | 20000 | | 2.98 | | 2.82 | 3.00 | | III | 0.16 | 0.02 | 26.4 | 3.3 | 0 | 0.564 | 0.036 | 0.400 | 0.436 | |
| 2.50% | 25000 | | 2.96 | | | 3.12 | | II | 2.96 | 0.16 | | 26.1 | NA | 0 | 0.624 | 0.376 | 1.000 | |
| 3.00% | 30000 | | 2.98 | | 2.65 | 3.01 | | III | 0.33 | 0.03 | 54.5 | 5.0 | 0 | 0.530 | 0.072 | 0.398 | 0.470 | |
| 3.50% | 35000 | | 2.96 | | | 3.00 | | II | 2.96 | 0.04 | | 6.5 | NA | 0 | 0.600 | 0.400 | 1.000 | |
| 4.00% | 40000 | | 2.99 | | | 3.01 | | II | 2.99 | 0.02 | | 3.3 | NA | 0 | 0.602 | 0.398 | 1.000 | |
| 4.50% | 45000 | | 3.07 | | | 3.10 | | II | 3.07 | 0.03 | | 5.2 | NA | 0 | 0.620 | 0.380 | 1.000 | |
| 5.00% | 50000 | | 2.99 | | | 3.03 | | II | 2.99 | 0.04 | | 6.6 | NA | 0 | 0.606 | 0.394 | 1.000 | |

| Salinity (wt % Na2CO3) | (ppm Na2CO3) | Hydrocarbon Level | Aqueous Level | Top of emulsion | Top Interface | Bottom Interface | Bottom of emulsion | Type | Volume of Oil Solubilized (cc) | Volume of Water Solubilized (cc) | Oil Sol. Ratio (cc/cc) | Water Sol. Ratio (cc/cc) | HC Sol. (mg/L) | Volume Fraction of Oil ($V_o$) | Volume Fraction of Microemulsion ($V_{me}$) | Volumn Fraction of Water ($V_w$) | $V_w + V_{me}$ |
|---|---|---|---|---|---|---|---|---|---|---|---|---|---|---|---|---|---|
| Reading: | | 5 days | Dec. 15, 2009 | | | | | | | | | | | | | | |
| 0.50% | 5000 | | 2.99 | | 2.78 | 3.11 | | III | 0.21 | 0.12 | 34.8 | 19.9 | 0 | 0.556 | 0.066 | 0.378 | 0.444 |
| 1.00% | 10000 | | 2.95 | | 2.56 | 3.29 | | III | 0.39 | 0.34 | 63.4 | 55.3 | 0 | 0.512 | 0.146 | 0.342 | 0.488 |
| 1.50% | 15000 | | 2.98 | | 2.70 | 3.29 | | III | 0.28 | 0.31 | 46.2 | 51.2 | 0 | 0.540 | 0.118 | 0.342 | 0.460 |
| 2.00% | 20000 | | 2.98 | | 2.80 | 3.11 | | III | 0.18 | 0.13 | 29.7 | 21.5 | 0 | 0.560 | 0.062 | 0.378 | 0.440 |
| 2.50% | 25000 | | 2.96 | | | 3.21 | | II | 2.96 | 0.25 | | 40.8 | NA | 0 | 0.642 | 0.358 | 1.000 |
| 3.00% | 30000 | | 2.98 | | | 3.10 | | II | 2.98 | 0.12 | | 19.8 | NA | 0 | 0.620 | 0.380 | 1.000 |
| 3.50% | 35000 | | 2.96 | | | 3.01 | | II | 2.96 | 0.05 | | 8.2 | NA | 0 | 0.602 | 0.398 | 1.000 |
| 4.00% | 40000 | | 2.99 | | | 3.01 | | II | 2.99 | 0.02 | | 3.3 | NA | 0 | 0.602 | 0.398 | 1.000 |
| 4.50% | 45000 | | 3.07 | | | 3.09 | | II | 3.07 | 0.02 | | 3.5 | NA | 0 | 0.618 | 0.382 | 1.000 |
| 5.00% | 50000 | | 2.99 | | | 3.00 | | II | 2.99 | 0.01 | | 1.7 | NA | 0 | 0.600 | 0.400 | 1.000 |

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

U.S. Pat. No. 4,842,776: Styrylaryloxy Ether Sulfonates, A Process for their Preparation and their Use in the Recovery of Crude Oil.
WIPO Patent Application WO/2008/079855: Enhanced Oil Recovery Systems and Consumer Products Containing Secondary Alcohol Derivatives.
U.S. Patent Application No. 20090270281: Use of Surfactant Mixtures for Tertiary Mineral Oil Extraction.

What is claimed is:

1. An alkoxy sulfate surfactant comprising one or more, poly propoxy groups (PO), poly ethoxy groups (EO) or both and a sulfate group of formula (I):

$$(C_6H_5CH_2CH_2)_a\text{—}C_6H_bO\text{—}PO_x\text{-}EO_y\text{—}SO_3^-M^+ \quad (I)$$

wherein a=3, b=2, a=2, b=3 or a=2-3, b=3-2;
wherein x corresponds to the number of propoxy groups and ranges from 1 to 50;
wherein y corresponds to the number of ethoxy groups and ranges from 0 to 100;
wherein M is a counter ion to the sulfate group, wherein M is selected from the group consisting of Na, K, Mg, Ca, and $NH_4$.

2. The composition of claim 1, wherein the composition is adapted for enhanced oil recovery (EOR) or environmental ground water cleanup.

3. The composition of claim 1, wherein the surfactant composition is added to a downhole fluid for EOR.

4. The composition of claim 1, wherein x is 1, 2, 3, 4, 5, 6, 7, 8, 9, 10, 12, 14, 16, 18, 20, 21, 22, 23, 24, 25, 30, 35, 40, 45, or 50.

5. The composition of claim 1, wherein y is 0 and x is 1, 2, 3, 4, 5, 6, 7, 8, 9, 10, 12, 14, 16, 18, 20, 21, 22, 23, 24, 25, 30, 35, 40, 45 or 50.

6. The composition of claim 1, wherein y is 0, 1, 2, 3, 4, 5, 6, 7, 8, 9, 10, 15, 20, 25, 30, 35, 40, 45, 50, 60, 70, 80, 90, or 100.

7. The composition of claim 1, wherein the alkoxy sulfate surfactant has a formula $(C_6H_5CH_2CH_2)_3\text{—}C_6H_2O\text{—}PO_7\text{-}EO_{10}\text{—}SO_3^-$.

8. The composition of claim 1, wherein the alkoxy sulfate surfactant has a formula $(C_6H_5CH_2CH_2)_2\text{—}C_6H_3O\text{—}PO_7\text{-}EO_{10}\text{—}SO_3^-$.

9. A method for making an alkoxy sulfate surfactant of formula (I) comprising the steps of:

$$(C_6H_5CH_2CH_2)_a\text{—}C_6H_bO\text{—}PO_x\text{-}EO_y\text{—}SO_3^- \quad (I)$$

alkoxylating a styrylphenol with a propylene oxide $(PO)_x$ group, an ethylene oxide $(EO)_y$ group or both in the presence of a basic catalyst, wherein a=3, b=2, a=2, b=3 or a=2-3, b=3-2, wherein x corresponds to the number of propoxy groups and ranges from 0 to 50, wherein y corresponds to the number of ethoxy groups and ranges from 0 to 100; and
sulfating the alkoxylated styrylphenol by a sulfamic acid sulfation process to make the styrylphenol alkoxy sulfate surfactant.

10. The method of claim 9, wherein the alkoxy sulfate surfactant is adapted for enhanced oil recovery (EOR) or environmental ground water cleanup.

11. The method of claim 9, wherein the styrylphenol alkoxy sulfate is added to a downhole fluid for EOR.

12. The method of claim 9, wherein x is 1, 2, 3, 4, 5, 6, 7, 8, 9, 10, 12, 14, 16, 18, 20, 21, 22, 23, 24, 25, 30, 35, 40, 45, or 50.

13. The method of claim 9, wherein y is 0 and x is 1, 2, 3, 4, 5, 6, 7, 8, 9, 10, 12, 14, 16, 18, 20, 21, 22, 23, 24, 25, 30, 35, 40, 45 or 50.

14. The method of claim 9, wherein y is 0, 1, 2, 3, 4, 5, 6, 7, 8, 9, 10, 15, 20, 25, 30, 35, 40, 45, 50, 60, 70, 80, 90, or 100.

15. The method of claim 9, wherein basic catalyst is KOH, NaOH, $NH_4OH$, LiOH or any combinations thereof.

16. The method of claim 9, wherein the alkoxy sulfate surfactant comprises a counter-ion to a sulfate group, wherein the counter-ion is selected from the group consisting of Na, K, Mg, Ca, and $NH_4$.

17. The method of claim 9, wherein the styrylphenol alkoxy sulfate surfactant has a formula $(C_6H_5CH_2CH_2)_3$—$C_6H_2O$—$PO_7$-$EO_{10}$—$SO_3^-$.

18. The method of claim 9, wherein the styrylphenol alkoxy sulfate surfactant has a formula $(C_6H_5CH_2CH_2)_2$—$C_6H_3O$—$PO_7$-$EO_{10}$—$SO_3^-$.

19. A method of making a tristyrylphenol (TSP) alkoxy sulfate surfactant having a formula $(C_6H_5CH_2CH_2)_3$—$C_6H_2O$—$PO_7$-$EO_{10}$—$SO_3^-$ comprising the steps of:
   propoxylating the TSP with propylene oxide (PO) in the presence of a basic catalyst selected from the group consisting of KOH, NaOH, $NH_4OH$, LiOH and any combination thereof, to form a propoxylated TSP (TSP-7PO), wherein a mole ratio of the TSP:PO is 1:7;
   ethoxylating the propoxylated TSP with a ethylene oxide (EO) in the presence of said basic catalyst to form a TSP-7PO-10EO, wherein the mole ratio of the TSP-7PO:EO is 1:10; and
   sulfating the TSP-7PO-10EO by a sulfamic acid sulfation process to make the TSP alkoxy sulfate surfactant having the formula $(C_6H_5CH_2CH_2)_3$—$C_6H_2O$—$PO_7$-$EO_{10}$—$SO_3^-$.

20. The method of claim 19, wherein the TSP alkoxy sulfate surfactant of formula $(C_6H_5CH_2CH_2)_3$—$C_6H_2O$—$PO_7$-$EO_{10}$—$SO_3^-$ is adapted for enhanced oil recovery (EOR) or environmental ground water cleanup.

21. A composition for enhanced oil recovery (EOR) or environmental ground water cleanup comprising:
   one or more alkoxy sulfate surfactants, wherein the one or more alkoxy sulfate surfactants have a general formula $(C_6H_5CH_2CH_2)_a$—$C_6H_bO$—$PO_x$-$EO_y$-$SO_3^-M^+$, wherein a=3, b=2, a=2, b=3 or a=2-3, b=3-2, wherein x corresponds to the number of propoxy groups and ranges from 0 to 50, wherein y corresponds to the number of ethoxy groups and ranges from 0 to 100, wherein M is a counter ion to a sulfate group, wherein M is selected from the group consisting of Na, K, Mg, Ca, and $NH_4$;
   one or more alkalinity generating agents; and
   a solvent.

22. The composition of claim 21, wherein the one or more alkalinity generating agents comprise alkali earth metal hydroxides, NaOH, KOH, LiOH, $NH_4OH$, $Na_2CO_3$, $NaHCO_3$, Na-metaborate, sodium silicate, sodium orthosilicate, $EDTANa_4$ or any combinations thereof.

23. The composition of claim 21, wherein the solvent comprises water, hard brine, hard water, polymer containing solutions, gas foam or any combinations thereof.

24. The composition of claim 21, wherein the composition is adapted for use alone, in an alkaline-surfactant-polymer formulation or in a gas foam for EOR applications.

25. The composition of claim 21, wherein the composition contains 0.1%, 0.5%, 1%, 2%, 3%, 4%, or 5% of the one or more alkalinity generating agents.

26. The composition of claim 21, wherein x is 1, 2, 3, 4, 5, 6, 7, 8, 9, 10, 12, 14, 16, 18, 20, 21, 22, 23, 24, 25, 30, 35, 40, 45, or 50.

27. The composition of claim 21, wherein y is 0 and x is 1, 2, 3, 4, 5, 6, 7, 8, 9, 10, 12, 14, 16, 18, 20, 21, 22, 23, 24, 25, 30, 35, 40, 45 or 50.

28. The composition of claim 21, wherein y is 0, 1, 2, 3, 4, 5, 6, 7, 8, 9, 10, 15, 20, 25, 30, 35, 40, 45, 50, 60, 70, 80, 90, or 100.

29. The composition of claim 21, wherein the alkoxy sulfate surfactant has a formula $(C_6H_5CH_2CH_2)_3$—$C_6H_2O$—$PO_7$-$EO_{10}$—$SO_3^-$.

30. The composition of claim 21, wherein the alkoxy sulfate surfactant has a formula $(C_6H_5CH_2CH_2)_2$—$C_6H_3O$—$PO_7$-$EO_{10}$—$SO_3^-$.

31. The composition of claim 21, wherein the composition is adapted for EOR from a crude oil, wherein the crude oil comprises paraffin based crude oils, asphaltene based crude oils or combinations and mixtures thereof.

32. The composition of claim 21, wherein the composition is adapted for EOR from an asphaltene based crude oil.

33. A method of enhanced oil recovery (EOR) from a hydrocarbon bearing formation comprising the steps of:
   injecting an alkoxy sulfate surfactant composition having a general formula $(C_6H_5CH_2CH_2)_a$—$C_6H_bO$—$PO_x$-$EO_y$—$SO_3^-M^+$, wherein a=3, b=2, a=2, b=3 or a=2-3, b=3-2, wherein x corresponds to the number of propoxy groups and ranges from 0 to 50, wherein y corresponds to the number of ethoxy groups and ranges from 0 to 100, wherein M is a counter ion to a sulfate group, wherein M is selected from the group consisting of Na, K, Mg, Ca, and $NH_4$, alone, as an alkaline-surfactant-polymer formulation (ASP) or in a gas foam into the hydrocarbon bearing formation at a temperature from 25 to 120° C., wherein the alkoxy sulfate surfactant composition is in water, hard water or hard brine and comprises greater than 0.05% of one or more alkalinity generating agents; and
   injecting a polymer push solution or the gas foam to recover the oil.

34. The method of claim 33, wherein the one or more alkalinity generating agents comprise alkali earth metal hydroxides, NaOH, KOH, LiOH, $NH_4OH$, $Na_2CO_3$, $NaHCO_3$, Na-metaborate, sodium silicate, sodium orthosilicate, $EDTANa_4$ or any combinations thereof.

35. The method of claim 33, wherein x is 1, 2, 3, 4, 5, 6, 7, 8, 9, 10, 12, 14, 16, 18, 20, 21, 22, 23, 24, 25, 30, 35, 40, 45, or 50.

36. The method of claim 33, wherein y is 0 and x is 1, 2, 3, 4, 5, 6, 7, 8, 9, 10, 12, 14, 16, 18, 20, 21, 22, 23, 24, 25, 30, 35, 40, 45 or 50.

37. The method of claim 33, wherein y is 0, 1, 2, 3, 4, 5, 6, 7, 8, 9, 10, 15, 20, 25, 30, 35, 40, 45, 50, 60, 70, 80, 90, or 100.

38. The method of claim 33, wherein the alkoxy sulfate surfactant has a formula $(C_6H_5CH_2CH_2)_3$—$C_6H_2O$—$PO_7$-$EO_{10}$—$SO_3^-$.

39. The method of claim 33, wherein the alkoxy sulfate surfactant has a formula $(C_6H_5CH_2CH_2)_2$—$C_6H_3O$—$PO_7$-$EO_{10}$—$SO_3^-$.

40. The method of claim 33, wherein the hydrocarbon bearing formation comprises one or more paraffin based crude oils, asphaltene based crude oils or combinations and mixtures thereof.

41. The method of claim 33, wherein the hydrocarbon bearing formation comprises an asphaltene based crude oil.

42. A non-ionic surfactant composition of formula (II) comprising an alkoxy group, wherein the alkoxy groups are selected from the group consisting of a poly propoxy (PO) and a poly ethoxy (EO) group $$(C_6H_5CH_2CH_2)_a\text{---}C_6H_bO\text{---}PO_x\text{-}EO_y \qquad (II)$$

wherein a=3, b=2, a=2, b=3 or a=2-3, b=3-2;

wherein x corresponds to the number of propoxy groups and ranges from 1 to 50;

wherein y corresponds to the number of ethoxy groups and ranges from 0 to 100.

43. The composition of claim 42, wherein the composition is adapted for enhanced oil recovery (EOR) or environmental ground water cleanup.

44. A method for making a non-ionic surfactant of formula (II) comprising an alkoxy group, wherein the alkoxy groups are selected from the group consisting of a poly propoxy (PO) and a poly ethoxy (EO) group comprising the step of $$(C_6H_5CH_2CH_2)_a\text{---}C_6H_bO\text{---}PO_x\text{-}EO_y \qquad (II)$$

alkoxylating a styrylphenol with a propylene oxide $(PO)_x$ group, an ethylene oxide $(EO)_y$ group or both in the presence of a basic catalyst, wherein a=3, b=2, a=2, b=3 or a=2-3, b=3-2, wherein x corresponds to the number of propoxy groups and ranges from 0 to 50, wherein y corresponds to the number of ethoxy groups and ranges from 0 to 100.

45. The method of claim 44, wherein the non-ionic surfactant is adapted for enhanced oil recovery (EOR) or environmental ground water cleanup.

46. A method for recovering an asphaltene based crude oil from a hydrocarbon bearing formation comprising the steps of:

injecting an alkoxy sulfate surfactant composition having a general formula $(C_6H_5CH_2CH_2)_a\text{---}C_6H_bO\text{---}PO_x\text{-}EO_y\text{---}SO_3^-M^+$, wherein a=3, b=2, a=2, b=3 or a=2-3, b=3-2, wherein x corresponds to the number of propoxy groups and ranges from 0 to 50, wherein y corresponds to the number of ethoxy groups and ranges from 0 to 100, wherein M is a counter ion to a sulfate group, wherein M is selected from the group consisting of Na, K, Mg, Ca, and $NH_4$, alone, as an alkaline-surfactant-polymer formulation (ASP) or a gas foam into the hydrocarbon bearing formation at a temperature from 25 to 120° C., wherein the alkoxy sulfate surfactant composition is in water, hard water or hard brine and comprises greater that 0.05% of one or more alkalinity generating agents; and injecting a polymer push solution or the gas foam to recover the oil.

47. The method of claim 46, wherein the one or more alkalinity generating agents comprise alkali earth metal hydroxides, NaOH, KOH, LiOH, $NH_4OH$, $Na_2CO_3$, $NaHCO_3$, Na-metaborate, sodium silicate, sodium orthosilicate, $EDTANa_4$ or any combinations thereof.

48. The method of claim 46, wherein x is 1, 2, 3, 4, 5, 6, 7, 8, 9, 10, 12, 14, 16, 18, 20, 21, 22, 23, 24, 25, 30, 35, 40, 45, or 50.

49. The method of claim 46, wherein y is 0 and x is 1, 2, 3, 4, 5, 6, 7, 8, 9, 10, 12, 14, 16, 18, 20, 21, 22, 23, 24, 25, 30, 35, 40, 45 or 50.

50. The method of claim 46, wherein y is 0, 1, 2, 3, 4, 5, 6, 7, 8, 9, 10, 15, 20, 25, 30, 35, 40, 45, 50, 60, 70, 80, 90, or 100.

51. The method of claim 46, wherein the alkoxy sulfate surfactant has a formula $(C_6H_5CH_2CH_2)_3\text{---}C_6H_2O\text{---}PO_7\text{-}EO_{10}\text{---}SO_3^-$.

52. The method of claim 46, wherein the alkoxy sulfate surfactant has a formula $(C_6H_5CH_2CH_2)_2\text{---}C_6H_3O\text{---}PO_7\text{-}EO_{10}\text{---}SO_3^-$.

53. The composition of claim 21, further comprising a co-surfactant.

54. The composition of claim 53, wherein said co-surfactant is an olefin sulfonate.

55. The method of claim 54, wherein said olefin sulfonate is a $C_{10}\text{-}C_{30}$ internal olefin sulfate (IOS).

56. Te method of claim 33, wherein said alkoxy sulfate surfactant composition further comprises a co-surfactant.

57. The method of claim 56, wherein said co-surfactant is an olefin sulfonate.

58. The method of claim 57, wherein said olefin sulfonate is a $C_{10}\text{-}C_{30}$ internal olefin sulfate (IOS).

59. The method of claim 46, wherein said alkoxy sulfate surfactant composition further comprises a co-surfactant.

60. The method of claim 59, wherein said co-surfactant is an olefin sulfonate.

61. The method of claim 60, wherein said olefin sulfonate is a $C_{10}\text{-}C_{30}$ internal olefin sulfate (IOS).

* * * * *